United States Patent [19]
DeMello et al.

[11] Patent Number: 5,429,597
[45] Date of Patent: Jul. 4, 1995

[54] KINK RESISTANT BALLOON CATHETER AND METHOD FOR USE

[75] Inventors: Richard DeMello, Acton; Andrew Kapravy, Stoughton; George T. Roberts, Weston; Sally Thornton, Marlborough, all of Mass.

[73] Assignee: Boston Scientific Corporation, Watertown, Mass.

[21] Appl. No.: 204,626

[22] Filed: Mar. 1, 1994

[51] Int. Cl.⁶ .......................................... A61M 31/00
[52] U.S. Cl. ................................ 604/49; 604/96; 604/282; 606/194
[58] Field of Search ...................... 128/656–658, 128/772; 606/192, 194; 604/49, 53, 96, 280, 282

[56] References Cited

U.S. PATENT DOCUMENTS

| | | | |
|---|---|---|---|
| 4,906,241 | 3/1990 | Noddin et al. | 606/194 |
| 4,932,419 | 6/1990 | de Toledo | 128/772 |
| 5,060,660 | 10/1991 | Gambale et al. | 128/772 |
| 5,141,518 | 8/1992 | Hess et al. | 606/194 |
| 5,144,959 | 9/1992 | Gambale et al. | 128/772 |
| 5,209,727 | 5/1993 | Radisch, Jr. et al. | 604/96 |
| 5,328,472 | 7/1994 | Steinke et al. | 604/102 |
| 5,348,537 | 9/1994 | Wiesner et al. | 604/96 |

*Primary Examiner*—Corrine Maglione
*Attorney, Agent, or Firm*—Frances P. Craig

[57] ABSTRACT

A kink resistant balloon catheter for insertion into a bodily conduit. The catheter (10) includes a shaft (20), a radiopaque distal tip (35), a dilatation balloon (33) between the shaft and the distal tip, and a removable core wire (40). The shaft includes a kink resistant, cross-wound multifilar (CWMF) coil (21) enclosed by a polymeric sleeve (22) and defining a central lumen (28) for delivery of a fluid inflation medium for inflating the balloon. A fixed core wire (36) interconnects the CWMF coil and the distal tip. In a method for widening constricted bodily passages using the novel balloon catheter, the removable core wire is inserted to assist positioning of the catheter, and is removed to permit rapid inflation and deflation of the balloon.

11 Claims, 2 Drawing Sheets

FIG. I

KINK RESISTANT BALLOON CATHETER AND METHOD FOR USE

BACKGROUND OF THE INVENTION

The present invention relates to catheters that can be placed in bodily conduits. The invention particularly relates to coronary dilatation catheters for use in administering treatments to widen constricted blood flow passages typically caused by stenoses in, for example, heart valves or coronary arteries.

A stenosis is a region of a blood vessel which has been narrowed to such a degree that blood flow is restricted. If the stenosis is severe, treatment is required to restore adequate blood flow, and often such treatment requires surgery or angioplasty. Transluminal angioplasty is a procedure for treating a patient having a stenosis or constricted region in a coronary artery. Frequently the stenosis can be expanded so that the artery will permit an acceptable blood flow rate.

Coronary angioplasty includes the insertion of a balloon catheter through a patient's artery to the arterial stenosis and injecting a suitable fluid into the balloon to inflate it. The inflated balloon expands the stenosis radially outwardly and compressing it against the artery wall to increase the cross-sectional area of the artery so that the artery has an acceptable blood flow rate. Angioplasty has become a successful alternative to coronary arterial bypass surgery.

Ordinary balloon catheters have a balloon fastened around the exterior of a tubular shaft, with the balloon in fluid flow relation with the interior of the shaft. The shaft provides a conduit for fluid inflation medium to inflate the balloon.

Known, so-called "balloon-on-a-wire" catheter devices are designed using a thin walled steel tube with a small diameter core wire, e.g. of solid steel, extending from its proximal end to its distal end. The distal end of the angioplasty balloon is attached near the distal end of the core wire, and a plastic sleeve extending over the core wire covers a joint between the proximal end of the balloon and the distal end of the steel tube. In such a catheter, the steel tube acts as the shaft of the device to provide pushability and torque to the core wire. The distal segment of the catheter, including the core wire, balloon, and sleeve extension, acts as the flexible portion of the device, capable of traversing tortuous anatomies.

One of the greatest disadvantages of this known design is the stiffness of the shaft tubing, which can result in difficulty in negotiating tortuous anatomies. Additionally, the thin walled steel tubing has a tendency to kink too easily during the process of pushing the catheter to thread it through the arteries. This kinking can lead to fracturing and separation at the kink points in the steel tubing. The stiffness of the tubing also reduces the uniformity of the torque rotation of the shaft in a curved or bent configuration. In this design, there is also an abrupt transition between the stiff shaft portion and the flexible distal portion of the catheter.

In some variations of this balloon-on-a-wire design, the distal core wire is allowed to extend completely through the inside diameter of the proximal tube to strengthen and reinforce the tubing and to act as a safety wire within the device in case of catastrophic failure of the catheter, for example complete fracture of the shaft. However, the presence of this core wire reduces the cross-sectional area of the lumen within the shaft available for inflation of the balloon. The presence of the core wire also dramatically increases the exposed surface area within the lumen, resulting in increased fluid drag and pressure loss along the length of the lumen. The decreases in both cross-sectional area and inflation pressure result in a significant increase in the time required to inflate and deflate the balloon which, in turn, limits its maximum practicable size.

In another context, medical devices are known which employ highly flexible coils, including cross-wound multifilar (CWMF) coils. For example, a CWMF coil may be used as a flexible guidewire tip to facilitate manipulation of a medical device into a selected precise position within a bodily passage. Alternatively, a known catheter-like guidewire includes a CWMF coil and a core wire. The CWMF coil is sheathed in a polymeric jacket to within a short distance from the distal tip of the device. Fluid medication may be administered to a bodily passage by seepage from a central lumen through the CWMF coil. This device is not intended for dilatation, and includes no dilatation balloon. Even if such a balloon were added at the distal region of the device, the seepage mechanism would not provide sufficiently rapid inflation and deflation of the balloon.

It would be desirable to have a balloon-on-a-wire type of dilatation catheter which is kink-resistant, is easily maneuvered through tortuous anatomies, provides improved safety and torqueability, and permits rapid inflation and deflation of the dilatation balloon and larger balloon sizes. The catheter described herein was developed to address that need.

SUMMARY OF THE INVENTION

In accordance with one aspect of the invention, a catheter for insertion into a bodily conduit includes a shaft having a proximal and a distal end. The shaft includes a cross-wound multifilar (CWMF) coil, a lumen internal to the CWMF coil for delivery of fluid inflation media, and a fluid impermeable flexible sleeve encasing the CWMF coil. The CWMF coil includes inner and outer multifilar coils. The inner coil is wound in an opposite pitch direction to that of the outer coil, and is disposed within the outer coil. The catheter also includes a dilatation balloon including a distal end, a proximal end fixed to the shaft distal end, and a balloon wall interconnecting the proximal and distal balloon ends. The balloon defines a chamber in fluid communication with the shaft lumen. The catheter further includes a removable core wire, a fixed core wire, and a distal tip, the fixed core wire fixed to and extending between a distal end of the CWMF coil and the distal tip through the balloon chamber. The distal tip is fixed to the fixed core wire and extends distally from the balloon distal end. The removable core wire has a diameter selected to removably fit within the lumen and has a length selected to extend the full length of the lumen and to protrude from the shaft proximal end.

In a narrower aspect, the inner coil of the CWMF coil extends beyond the outer coil at its distal end, forming a stepped portion of the shaft of a sufficient axial length for the balloon first end to be fixed to the shaft at the stepped portion.

In another aspect, the invention is a method for widening a constriction within a bodily conduit. The method involves positioning the dilatation balloon of the catheter in accordance with the invention at the constriction within the bodily conduit. The positioning is accomplished by manipulating the catheter within the bodily conduit by pushing, pulling, and torquing the shaft proximal end while varying the stiffness of the shaft distal end, as necessary, by partially withdrawing the removable core wire from and reinserting the removable core wire into the shaft distal end. The removable core wire is then removed from the lumen after the dilatation balloon is positioned at the constriction within the bodily conduit to provide an open lumen for inflation and deflation of the dilatation balloon. The dilatation balloon is then inflated with the inflation medium via the open lumen to widen the constriction, and deflated via the open lumen.

BRIEF DESCRIPTION OF THE DRAWINGS

For a better understanding of the present invention, together with other objects, advantages, and capabilities thereof, reference is made to the following Description and appended Claims, together with the Drawings in which:

DETAILED DESCRIPTION OF THE PREFERRED EMBODIMENTS

Figure 1:
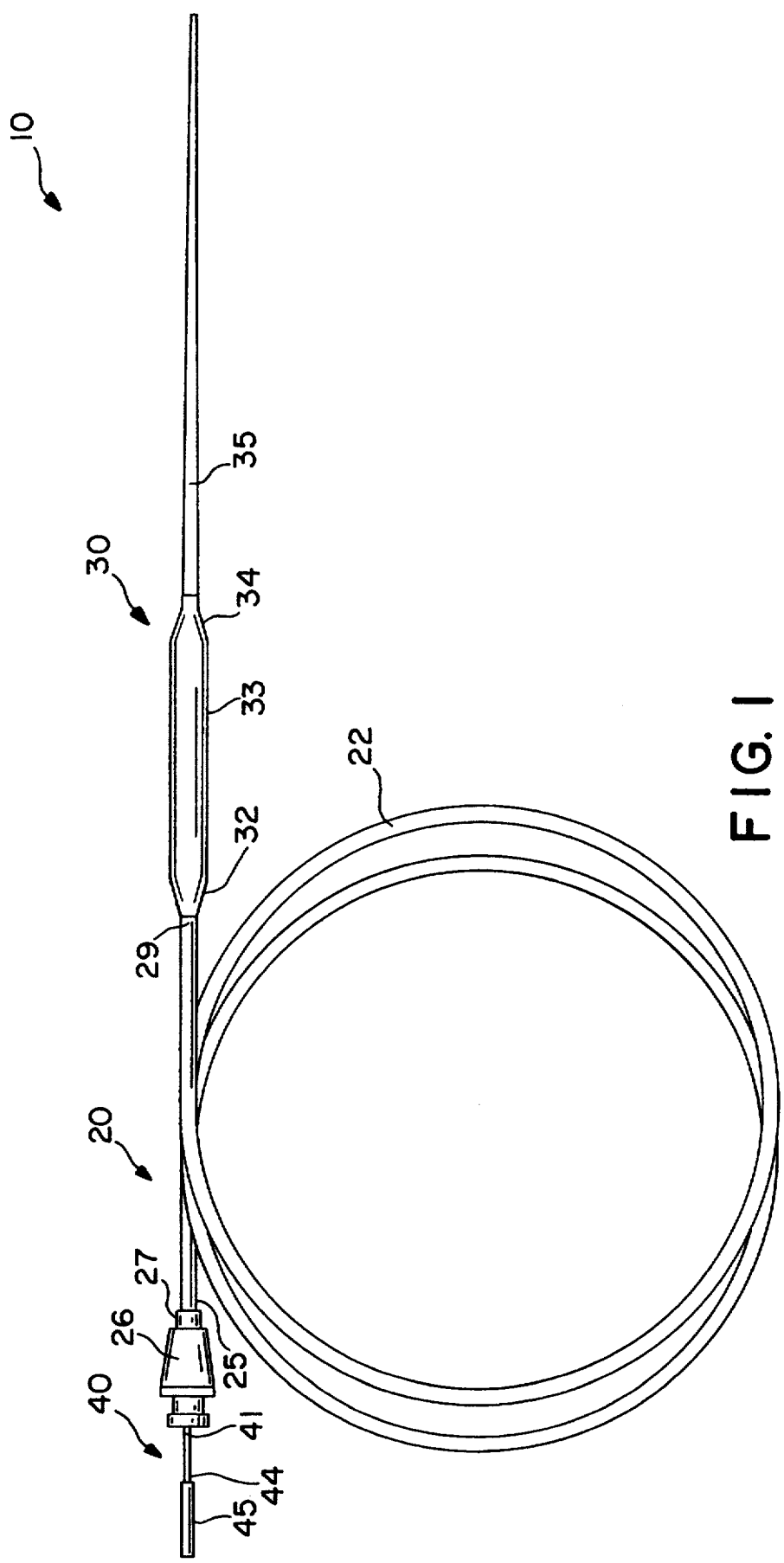
FIG. 1 is a elevation view of a balloon catheter in accordance with one embodiment of the present invention.

An exemplary embodiment of the catheter in accordance with the invention is described herein. The removable core balloon-on-a-wire catheter includes an angioplasty balloon mounted at the distal end of a kink-resistant, cross-wound multifilar (CWMF) guidewire coil. A removable core wire is inserted into and threaded through the lumen formed within the CWMF coil by the hollow inside diameter of the coil.

A CWMF coil is an assembly of two separate multifilar helically wound coils, a smaller diameter, inner coil wound in one helical direction inserted into a larger diameter, outer coil wound in the opposite helical direction. Stainless steel is a typical material for fabricating the filaments of the CWMF coil. The filaments of each of the inner and outer coils may be of, e.g., circular, oval, square, or rectangular cross-section. In one embodiment, the filaments of the outer coil have a circular cross-section, while those of the inner coil are flat or rectangular in cross-section. The inner and outer coils are sized and fitted together so that the coils are in intimate contact with one another.

The helical coil construction of the CWMF coil provides a highly flexible shaft for the catheter, while the opposite pitch angles of the cross-wound inner and outer coils act to lock the coils against one another and to provide a high level of torque transmission during rotation of the CWMF coil. Additionally, the multifilar nature of each of the inner and outer coils, combined with their cross-winding to make up the CWMF coil, provides a high degree of tensile strength to the CWMF coil, eliminating the need for a safety wire extending the entire length of the catheter. The outer and inner diameters of the CWMF coil are selected to balance the requirements for strength, maneuverability, ease of passage through bodily lumens, and speed of balloon inflation and deflation. As with known catheters, the length of the CWMF coil of the shaft is largely determined by the length of catheter required to perform the desired medical procedure. Typically, the CWMF coil is encased in a sheath or jacket, for example the flexible sleeve described below.

As mentioned above, use of a CWMF coil as the catheter shaft provides kink resistance, high tensile strength, and high torque transmission for ease of manipulation of the catheter. However, the highly flexible nature of the CWMF coil can detract from the pushability of the catheter during such manipulation. A removable core wire extendable through the entire length of the CWMF coil provides support and pushability to the shaft during introduction and manipulation of the catheter device. Once the catheter is in position, the core wire can be completely removed from the lumen to allow for ease of balloon inflation and deflation.

The removable core wire described above is a flexible wire, although stiffer than the CWMF coil, and is typically of a generally circular cross-section and uniform diameter over most of its length. The wire may be formed from a nickel titanium alloy, e.g. "Nitinol", or from stainless steel or other strong, flexible material considered suitable for balloon catheter guidewires. The removable core is sized to move freely in an axial direction within the central lumen of the CWMF coil. Its length is such that, when fully inserted into the lumen and extending its entire length, it protrudes from the proximal end of the shaft for gripping and for adjustment of the length to which the removable core wire extends into the lumen. The removable core wire normally extends fully into the lumen to the proximal end of the CWMF coil for maximum stiffness and pushability of the shaft. However, it may be partially withdrawn temporarily to increase the flexibility of the distal portion of the shaft, for example during the maneuvering of the catheter through a particularly tortuous anatomy. In a preferred embodiment, the removable core wire is gradually tapered at its distal end to provide graduated flexibility at the shaft distal end. To ease the passage of the tapered end of this removable core wire through the lumen, the taper may be fashioned to end in, e.g., a ball-shaped tip. Conveniently, a handle may be affixed to the proximally protruding end of the removable core wire for ease of gripping and manipulation of the wire.

The proximal end of a dilatation balloon is fixed to the distal end of the shaft, e.g. by a suitable adhesive, in a manner suitable for permitting inflation of the balloon via the lumen in the CWMF coil. The balloon may be any conventional balloon material and design used in such catheters; for example, the balloon may be fabricated from polyethylene terephthalate or Nylon. The balloon distal end typically is fixed to a distal tip described in more detail below.

A fixed core wire extends axially through the balloon and is fixed to both the shaft and the distal tip to provide stability to the balloon while it is being maneuvered in its deflated state into position within, e.g., an artery. The fixed core wire may be stainless steel, and in one embodiment it carries one or more radiopaque markers to aid in the exact positioning of the balloon. The markers may be of any material conventionally used for such markers, e.g. tantalum or other radiopaque metal. In one embodiment, one end of the fixed core wire is soldered to the inside surfaces of the inner coil of the CWMF coil, partially obstructing the lumen at its distal end. The ball-shaped tip of the removable core wire may then be sized to prevent passage of the removable core beyond the obstructed lumen distal end into the balloon.

The distal tip may be any tip conventionally used in such catheters, for example a tapered metal or alloy wire or conical shape, or a highly flexible spring coil of, e.g., platinum wire. In an alternate, preferred embodiment, the tip may be fabricated from a polymeric material compounded with a radiopaque metallic powder to render the entire tip radiopaque. Also in a preferred embodiment, a tapered flexible tip at least as long as the balloon, to aid in maneuvering of the catheter, is fabricated by embedding an extension of the fixed core wire, i.e. a portion extending beyond the distal end of the balloon, within a molded plastic tip. The extension of the fixed core wire is tapered and, optionally, flattened to gradually increase its flexibility within the tip. A polymer, for example Nylon, polyethylene terephthalate, polyethylene, polyurethane, or other polymer with similar properties is blended with sufficient radiopaque powder, e.g. tungsten, tantalum, etc., to render the blend radiopaque, then molded about the fixed core extension into a shape suitable for a catheter distal tip. A typical ratio for the radiopaque powder in the tip is about 80 weight % tungsten in a Nylon, for example "Pebax ®" (Atochem, Inc.). Such a filled polymeric tip enables heat bonding of the polymeric balloon to the tip, provides a larger tip diameter at its distal end to further facilitate bonding to the balloon without increasing the stiffness of the tip, and further control over the graduated flexibility of the tip.

The preferred catheter has a length of about 40–200 cm and a nominal outside diameter of about 0.035". The preferred CWMF coil is about 35-195 cm long, with an inside diameter of about 0.010"–0.030" and an outside diameter of about 0.014"–0.038". Each individual filament of the inner and outer coils is preferably about 0.001"–0.008" in equivalent diameter, with preferably about 8 filaments in each multifilar coil. The preferred outside diameter for the removable core is about 0.006"–0.029", while that for the fixed core is about 0.004"–0.015". The preferred balloon is about 1–10 cm long and about 1–20 mm in outside diameter, with a wall thickness of about 0.0002"–0.0020". The distal tip is about 5–50 mm long with a diameter at the balloon distal end of about 0.010"–0.038".

The preferred shaft has a very close fitting, thin walled, polymeric sleeve, sheath, or jacket covering the entire outer surface of the CWMF coil. By the term "thin walled" jacket is meant a jacket having a wall thickness of about 0.001"–0.004". The jacket may be fabricated from, for example, Teflon ®, polyethylene terephthalate, or any other flexible polymeric material conventionally considered suitable for use in a balloon catheter and capable of application as a very thin coating or shrink-wrap covering for encasing a shaft of small diameter. A material found to be particularly suitable is a blend of 5 w/o (weight %) Selar ® in polyethylene terephthalate. The preferred method for application of the thin-walled jacket is to shrink-wrap a Teflon or other suitable polymeric sleeve about the CWMF coil. Alternatively, the jacket may be applied by dipping, spraying, etc. It is preferred that the entire catheter, including the polymeric sleeve, be impermeable to the fluid inflation medium to prevent leakage of the fluid during the dilatation procedure.

If desired, the outer surface of the balloon, tip, and jacketed shaft, or any portion thereof, may be coated with a hydrophilic coating or other low-friction coating to minimize friction during positioning of the catheter.

Figure 2:
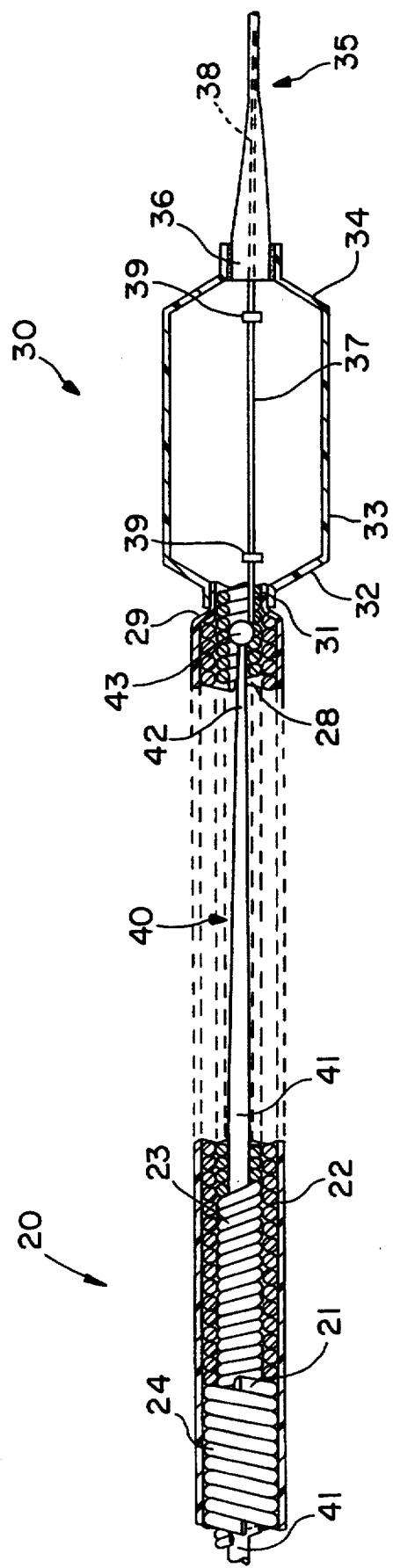
FIG. 2 is a elevation view, partly in cross-section, of a portion of the catheter of FIG. 1.

Referring now to FIGS. 1 and 2, not drawn to scale, catheter 10 in accordance with one embodiment of the present invention includes proximal shaft portion 20, distal portion 30, and removable core portion 40.

Shaft 20 includes cross-wound multifilar (CWMF) coil 21 covered by thin walled, shrink-wrapped polymeric jacket 22. The preferred CWMF coil 21 is fabricated by winding separate multifilar coils, inner coil 23 and outer coil 24, each made up of 8 adjacent filaments, at opposite pitch angles, as shown in FIG. 2. Coils 23 and 24 are fitted together with the coils in intimate contact with one another, the opposite pitch angles of coils 23 and 24 acting to lock the coils against one another and to provide a high level of torque transmission during rotation of CWMF coil 21. Additionally, the multifilar nature of each of coils 23 and 24, combined with the cross-winding of coils 23 and 24 in CWMF coil 22, provides a high degree of tensile strength to CWMF coil 22, eliminating the need for a safety wire within the catheter device.

CWMF coil 21 is encapsulated within thin wall polymeric jacket 22. Coils 23 and 24 and jacket 22 each terminate at proximal end 25 of shaft 20, and are enclosed at proximal end 25 by Luer fitting 26 and strain relief sleeve 27. Fitting 26 and sleeve 27 each are fastened to proximal end 25 with a suitable adhesive, providing a fluid-tight seal in known manner. The inside diameter of inner coil 23 defines central lumen 28, which extends throughout coil assembly 21.

Distal dilating portion 30 includes distal end 29 of shaft 20, at which inner coil 23 of CWMF coil 21 is permitted to slightly extend distally beyond outer coil 24. Jacket 22 encapsulates the extended portion of inner coil 23, providing stepped portion 31. Stepped portion 31 is sufficient in length, e.g. about 5 mm, to permit bonding of proximal end 32 of dilation balloon 33 to stepped portion 31 by a suitable adhesive in known manner to provide a fluid-tight seal. Distal end 34 of balloon 33 is bonded, for example, by heat sealing or by an adhesive to tungsten loaded Nylon distal tip 35 at its proximal end 36 to provide a fluid-tight seal. Balloon 33 may be inflated with a fluid inflation medium via fitting 26 and lumen 28. Fixed distal core wire 37 is bonded to the extended portion of inner coil 23, for example, by soldering.

Fixed core wire 37 extends from inner coil 23 through balloon 33 to tip 35. In the embodiment shown, tapered extension 38 of core wire 37 extends into distal tip 35 to provide graduated flexibility to the tip, as described above. Fixed core wire 37 may be fabricated from any material normally used for the balloon wire and extending guidewire of balloon-on-a-wire catheters. In a preferred embodiment, distal tip 35 is fabricated from a radiopaque polymer, for example a metal-filled polymer, as described above. Fixed core wire 37 has a uniform diameter from inner coil 23 through balloon 33, but preferably is tapered to a smaller diameter as it extends distally beyond balloon 33. Typically, core wire extension 38 tapers from 0.010" to 0.003" in diameter within distal tip 35. This tapering provides an extremely flexible distal tip to assist in threading the catheter through tortuous anatomies. Also in a preferred embodiment, two radiopaque markers 39 are attached to core wire 37 within balloon 33 to assist in proper placement of the balloon relative to a stenosis before inflation of the balloon. For some procedures, a hydrophilic coating (not shown) may be applied to any part or all of the outer surfaces of distal tip 35, balloon 33, and shaft 20 to reduce their coefficient of friction and ease proper placement of catheter 10.

Removable core portion 40 includes non-fixed, removable core wire 41, typically a flexible nickel-titanium alloy wire. Removable core wire 41 is separate from fixed core wire 37. Core wire 41 is of a diameter selected to fit within lumen 28, and is typically of a uniform diameter along most of its length and tapered to a smaller diameter at its distal end 42 to provide increased flexibility to distal end 42. Distal end 42 of core wire 41 ends in ball-shaped tip 43, providing smooth movement of removable core wire 41 within coil assembly 21. Tip 43 is sized to prevent core wire distal end 42 from passing beyond stepped portion 31 and into balloon 33. Proximal end 44 of removable core portion 40 includes handle 45, which is a polymeric jacket surrounding and bonded to removable core wire 41.

Typical materials useful for fabricating the catheter described herein, in addition to those mentioned above, are as follows: The strain relief sleeve, Luer fitting, and handle may be Nylon or other material known to be suitable for such features. The adhesive for bonding the balloon, radiopaque markers, Luer fitting, strain relief sleeve, and handle may be any adhesive considered suitable for use in balloon catheters, e.g. an epoxy adhesive for bonding the distal tip and a cyanoacrylate adhesive for the remaining features mentioned. Although the materials specifically mentioned herein have been used successfully, the invention is not limited to these materials.

In operation, the removable core wire is inserted into the lumen of the catheter coil assembly and is threaded through the lumen until its ball-shaped tip reaches the stepped portion of the shaft, where its passage is obstructed by the fixed core wire. The catheter device is inserted into, e.g., the vasculature of a patient, and is manipulated into position by torquing, pushing, and pulling. If desired, the removable core may be partially withdrawn within the lumen at any time during the insertion procedure to provide variable flexibility/stiffness along the length of the CWMF coil portion of the catheter. Once the catheter is in position, the removable core wire is removed from the device and an inflation syringe is connected to the Luer fitting. The balloon is inflated and deflated via the central lumen of the CWMF coil. If further positioning is desired, the inflation syringe may be removed from the Luer fitting and the removable core reinserted. Upon completion of the dilatation procedure, the catheter is removed from the patient.

This novel catheter presents the advantages of improved safety and maneuverability associated with the strength, flexibility, high torqueability, and kink-resistance of the shaft and the variable stiffness along the length of the shaft, all provided by the combination of the CWMF coil and the removable core wire, as described herein. The low friction outer surfaces provided by the jacket and, optionally, the low-friction coating also improve the maneuverability of the catheter. Additionally, with the removable core removed from the catheter, rapid inflation/deflation of the dilatation balloon is possible, decreasing the time required for the procedure and/or increasing the useable size of the dilatation balloon.

It is apparent that modifications and changes can be made within the spirit and scope of the present invention. It is our intention, however, only to be limited by the scope of the appended claims.

We claim:

1. A method for widening a constriction within a bodily conduit, said method comprising the steps of:
    positioning a dilatation balloon of a catheter at said constriction within said bodily conduit, said catheter comprising: (a) a shaft having a proximal end and a distal end and comprising a cross-wound multifilar coil, a lumen internal to said cross-wound multifilar coil for delivery of fluid inflation media, and a fluid impermeable flexible sleeve encasing said cross-wound multifilar coil, wherein said cross-wound multifilar coil comprises inner and outer multifilar coils, said inner coil being wound in an opposite pitch direction to that of said outer coil, said inner coil being disposed within said outer coil; (b) said dilatation balloon, wherein said dilatation balloon includes a distal end, a proximal end fixed to said shaft distal end, and a balloon wall interconnecting said proximal and distal balloon ends, said balloon defining a chamber in fluid communication with said lumen; (c) a fixed core wire having a proximal end immovably fixed directly to a distal end of said cross-wound multifilar coil; (d) a distal tip fixed to said fixed core wire and extending distally from said balloon distal end, said fixed core wire extending between a distal end of said cross-wound multifilar coil and said distal tip through said chamber; (e) a removable core wire of a diameter selected to removably fit within said lumen and of a length selected to extend the full length of said lumen and to protrude from said shaft proximal end;
    wherein said positioning step comprises manipulating said catheter within said bodily conduit by pushing, pulling, and torquing said shaft proximal end while varying the stiffness of said shaft distal end, as necessary, by partially withdrawing said removable core wire from and reinserting said removable core wire into said shaft distal end;
    removing said removable core wire from said lumen after said dilatation balloon is positioned at said constriction within said bodily conduit to provide an open lumen for inflation and deflation of said dilatation balloon;
    inflating said dilatation balloon with said inflation medium via said open lumen to widen said constriction; and
    deflating said dilatation balloon via said open lumen.

2. A catheter for insertion into a bodily conduit, said catheter comprising:
    a shaft having a proximal and a distal end and comprising a cross-wound multifilar coil, a lumen internal to said cross-wound multifilar coil for delivery of fluid inflation media, and a fluid impermeable flexible sleeve encasing said cross-wound multifilar coil, wherein said cross-wound multifilar coil comprises inner and outer multifilar coils, said inner coil being wound in an opposite pitch direction to that of said outer coil, said inner coil being disposed within said outer coil;
    a dilatation balloon including a distal end, a proximal end fixed to said shaft distal end, and a balloon wall interconnecting said proximal and distal balloon ends, said balloon defining a chamber in fluid communication with said lumen;
    a fixed core wire having a proximal end immovably fixed directly to a distal end of said cross-wound multifilar coil;

a distal tip fixed to said fixed core wire and extending distally from said balloon distal end, said fixed core wire extending between said distal end of said cross-wound multifilar coil and said distal tip through said chamber;

a removable core wire of a diameter selected to removably fit within said lumen and of a length selected to extend the full length of said lumen and to protrude from said shaft proximal end.

3. A catheter in accordance with claim 2 wherein said shaft further comprises fitting means at its proximal end for interconnection of inflation means to said lumen.

4. A catheter in accordance with claim 3 further comprising strain relief means between said fitting means and said flexible sleeve.

5. A catheter in accordance with claim 2 wherein said flexible sleeve comprises a polymeric sleeve about 0.001"–0.004" thick, shrink fitted to said cross-wound multifilar coil.

6. A catheter in accordance with claim 2 wherein said inner coil extends beyond said outer coil at its distal end, forming a stepped portion of said shaft of a sufficient axial length for said balloon first end to be fixed to said shaft at said stepped portion.

7. A catheter in accordance with claim 2 further comprising at least one radiopaque marker affixed to said fixed core wire within said chamber.

8. A catheter in accordance with claim 2 wherein said distal tip is fabricated from a radiopaque material comprising a polymeric material filled with a radiopaque metal powder.

9. A catheter in accordance with claim 2 wherein a distal end of said removable core wire is tapered to a smaller diameter in the distal direction.

10. A catheter in accordance with claim 9 further including a ball-shaped tip on the tapered portion of said removable core wire, the diameter of said ball-shaped tip being selected to permit passage of said ball-shaped tip through said lumen and to prevent passage of said ball-shaped tip past said fixed core wire into said chamber.

11. A catheter for insertion into a bodily conduit, said catheter comprising:

a proximal shaft comprising a cross-wound multifilar coil, a lumen internal to said cross-wound multifilar coil for delivery of fluid inflation media, a fluid tight, flexible polymeric sleeve encasing said cross-wound multifilar coil, fitting means at a proximal end of said shaft portion for interconnection of inflation means to said lumen, and strain relief means between said flexible sleeve and said fitting means, wherein said cross-wound multifilar coil comprises inner and outer multifilar coils, said inner coil being wound in an opposite pitch direction to that of said outer coil, said inner coil being disposed within said outer coil and generally coextensive therewith, but extending distally therebeyond to form a stepped portion of said shaft;

a dilatation balloon extending from a distal end of said shaft and including a proximal end fixed to said shaft, a distal end, and a generally cylindrical wall interconnecting said proximal and distal balloon ends, said balloon defining a chamber in fluid communication with said lumen;

a fixed core wire fixed to a distal end of said cross-wound multifilar coil;

at least one radiopaque marker affixed to said fixed core wire within said chamber;

a radiopaque distal tip fixed to said fixed core wire and extending distally from said balloon distal end, said fixed core wire extending between said distal end of said cross-wound multifilar coil and said distal tip through said chamber;

a removable core wire of a diameter selected to removably fit within said lumen and of a length selected to extend the full length of said lumen and to protrude from a proximal end of said shaft, a distal end of said removable core wire being tapered to a smaller diameter in the distal direction, said tapered portion including a ball-shaped tip, the diameter of said ball-shaped tip being selected to permit passage of said ball-shaped tip through said lumen and to prevent passage of said ball-shaped tip past said fixed core wire into said chamber.

* * * * *